United States Patent
He et al.

(10) Patent No.: US 11,582,386 B2
(45) Date of Patent: Feb. 14, 2023

(54) CONTROL METHOD, CONTROL SYSTEM, ELECTRONIC DEVICE AND READABLE STORAGE MEDIUM FOR CAPSULE ENDOSCOPE

(71) Applicants: ANKON TECHNOLOGIES CO., LTD, Wuhan (CN); ANX IP HOLDING PTE. LTD., Singapore (SG)

(72) Inventors: Weikang He, Wuhan (CN); Pan Zhou, Wuhan (CN); Qinghua Zhou, Wuhan (CN); Yi Li, Wuhan (CN); Yanli Liu, Wuhan (CN)

(73) Assignees: ANKON TECHNOLOGIES CO., LTD., Shanghai (CN); ANX IP HOLDING PTE. LTD., Singapore (SG)

( * ) Notice: Subject to any disclaimer, the term of this patent is extended or adjusted under 35 U.S.C. 154(b) by 0 days.

(21) Appl. No.: 17/150,788

(22) Filed: Jan. 15, 2021

(65) Prior Publication Data

US 2022/0232170 A1 Jul. 21, 2022

(51) Int. Cl.
*A61B 1/00* (2006.01)
*H04N 5/232* (2006.01)
(Continued)

(52) U.S. Cl.
CPC ..... *H04N 5/232411* (2018.08); *A61B 1/0002* (2013.01); *A61B 1/00006* (2013.01);
(Continued)

(58) Field of Classification Search
None
See application file for complete search history.

(56) References Cited

U.S. PATENT DOCUMENTS

| | | | |
|---|---|---|---|
| 2008/0045792 A1* | 2/2008 | Shimizu | A61B 1/00032 600/118 |
| 2008/0074491 A1* | 3/2008 | Matsui | A61B 1/00016 348/65 |

(Continued)

FOREIGN PATENT DOCUMENTS

| | | |
|---|---|---|
| CN | 101414884 A | 4/2009 |
| CN | 109302738 A | 2/2019 |

*Primary Examiner* — Howard D Brown, Jr.
(74) *Attorney, Agent, or Firm* — Treasure IP Group, LLC

(57) ABSTRACT

The present invention discloses a control method, system, electronic device and readable storage medium for a capsule endoscope. The method includes: providing a working apparatus, comprising a capsule endoscope, and an external data recorder for cooperating with and controlling the capsule endoscope; monitoring the received ambient power by the external data recorder before wireless transmission of the capsule endoscope or during an intermittence between two transmissions, and/or monitoring the output power of the capsule endoscope by the external data recorder as data is transmitted during wireless transmission; adjusting the operating state of the working apparatus according to the ambient power and/or output power. The present invention can monitor the power during the dormant period before image interaction and/or in the process of image interaction, thus adjust the operating state of the capsule endoscope in real time, which can improve the wireless communication performance and operating time of the capsule endoscope.

7 Claims, 6 Drawing Sheets

(51) Int. Cl.
*A61B 1/04* (2006.01)
*H04N 17/00* (2006.01)
*H04N 5/225* (2006.01)

(52) U.S. Cl.
CPC ...... *A61B 1/00016* (2013.01); *A61B 1/00029* (2013.01); *A61B 1/041* (2013.01); *H04N 17/002* (2013.01); *H04N 2005/2255* (2013.01)

(56) References Cited

U.S. PATENT DOCUMENTS

| | | | |
|---|---|---|---|
| 2009/0303319 A1* | 12/2009 | Sato | H04N 5/2256 348/335 |
| 2015/0011829 A1* | 1/2015 | Wang | A61B 1/045 600/118 |
| 2015/0031954 A1* | 1/2015 | Kimoto | A61B 1/00036 600/118 |
| 2017/0105610 A1* | 4/2017 | On | A61B 1/00009 |
| 2018/0365826 A1* | 12/2018 | Oh | A61B 5/7264 |
| 2019/0090721 A1 | 3/2019 | Koide | |
| 2021/0092328 A1* | 3/2021 | Miyazono | H04N 7/185 |
| 2021/0320783 A1* | 10/2021 | Masuda | H04L 7/0012 |
| 2021/0369093 A1* | 12/2021 | Duan | A61B 1/273 |

\* cited by examiner

CONTROL METHOD, CONTROL SYSTEM, ELECTRONIC DEVICE AND READABLE STORAGE MEDIUM FOR CAPSULE ENDOSCOPE

CROSS-REFERENCE OF RELATED APPLICATIONS

The application claims priority to Chinese Patent Application No. 202010042699.3 filed on Jan. 15, 2020, the contents of which are incorporated by reference herein.

FIELD OF INVENTION

The present invention relates to the field of medical equipment, and more particularly to a control method, control system, electronic device and readable storage medium for a capsule endoscope.

BACKGROUND

Capsule endoscope is a medical device that integrates core components such as a camera and a wireless transmission antenna into a capsule that can be swallowed by a subject. During the examination, as swallowed into the body of the subject, the capsule endoscope takes images in the digestive tract while transmits the images to the outside of the body for review and evaluation by a physician.

Existing capsule endoscopy systems communicate with a portable external data recorder through wireless electromagnetic waves, so that the images taken by the capsule can be effectively transmitted to the data recorder. Existing capsule endoscopy systems, because they cannot sense and monitor the wireless electromagnetic environment, can cause loss of images during transmission when there are external interference signals of the same frequency, and affect the integrity of the final medical diagnosis.

In addition, in an actual clinical examination, the body size of a subject varies greatly, with a waist circumference ranging from 60 cm to 150 cm. At the same time, the human tissue thickness and electrical parameters are different when the capsule endoscope passes through different parts of the digestive tract, which may impose different requirements on the communication link margin of the capsule endoscopy system, with a difference of 5-20 dB. The existing solution to such problem is to increase the radiation power of the capsule endoscope and the receiving sensitivity of the recorder, so as to cover the larger size of people as much as possible.

There are mainly two means to increase the radiation power of the capsule endoscope: one is to increase the RF output power of the capsule endoscope by adding a PA (abbreviation for Power Amplifier) chip. The capsule endoscope, as powered by a coin cell battery, is more sensitive to power consumption, so adding a PA chip to increase output power can greatly affect the working time of the capsule. Under the existing battery technology, this solution is not feasible due to the power consumption problem. The other is to optimize the antenna of the capsule endoscope to improve the gain performance of the antenna. However, the internal space of the capsule endoscope is so confined that it is difficult to improve the antenna gain by optimizing the antenna, and the space for improvement is limited.

SUMMARY OF THE INVENTION

In order to solve the above technical problems, the object of the present invention is to disclose a control method, control system, electronic device and a readable storage medium for a capsule endoscope.

It is one object of the present invention, to provide a control method for a capsule endoscope, the method comprising: providing a working apparatus, the working apparatus comprising: a capsule endoscope, and a portable external data recorder for cooperating with and controlling the capsule endoscope;

monitoring the received ambient power by the portable external data recorder before wireless transmission of the capsule endoscope or during an intermittence between two transmissions, and/or monitoring the output power of the capsule endoscope by the external data recorder as wireless data is transmitted in the process of wireless transmission;

adjusting the operating state of the working apparatus according to the ambient power and/or output power.

In an embodiment, "adjusting the operating state of the working apparatus according to the ambient power" specifically comprises:

determining whether the ambient power value monitored in a preset operating frequency band is greater than a preset ambient power threshold, determining that there is an interference signal, and switching the operating frequency and/or alarm of the working apparatus, when the ambient power value is greater than the preset ambient power threshold;

continuing monitoring when the ambient power value is not greater than the preset ambient power threshold.

In an embodiment, "adjusting the operating state of the working apparatus according to the ambient power" specifically comprises:

determining whether the ambient power values monitored in the preset operating frequency band within N consecutive communication cycles and/or within a continuous preset duration are all greater than a preset ambient power threshold, wherein N is a positive integer not less than 2 and the preset duration is not less than the duration of 2 communication cycles.

determining that there is an interference signal, and switching the operating frequency and/or alarm of the working apparatus, when the ambient power values are all greater than the preset ambient power threshold;

continuing monitoring when the ambient power values are not all greater than the preset ambient power threshold.

In an embodiment, "adjusting the operating state of the working apparatus according to the output power" specifically comprises:

determining the relationship between the magnitudes of the monitored output power value and a preset output power threshold; wherein the preset output power threshold comprises a preset first output power threshold and a preset second output power threshold, and the preset second output power threshold is less than the preset first output power threshold;

reducing the output power of the capsule endoscope when the monitored output power value is greater than the first output power threshold;

increasing the output power of the capsule endoscope when the monitored output power value is less than the second output power threshold;

maintaining the monitoring state when the monitored output power value is between the first output power threshold and the preset second output power threshold.

In an embodiment, a power amplifier chip is added to the capsule endoscope, and the method further comprises: starting the power amplifier chip when the output power of the capsule endoscope needs to be increased.

It is another object of the present invention, to provide an electronic device, comprising a memory and a processor. The memory stores a computer program that run on the processor, and the processor executes the program to implement the steps of the control method for capsule endoscope described above.

It is still another object of the present invention, to provide a computer-readable storage medium for storing a computer program. The computer program is executed by the processor to implement the steps of the control method for capsule endoscope described above.

It is yet another object of the present invention, to provide a control system for a capsule endoscope, the system comprising: a working apparatus, the working apparatus comprising: a capsule endoscope, and a portable external data recorder for cooperating with and controlling the capsule endoscope;

a monitoring module, used for monitoring the received ambient power by the portable external data recorder before wireless transmission of the capsule endoscope or during an intermittence between two transmissions, and/or monitoring the output power of the capsule endoscope by the external data recorder as wireless data is transmitted in the process of wireless transmission;

an adjustment output module, used for adjusting the operating state of the working apparatus according to the ambient power and/or output power.

In an embodiment, when adjusting the operating state of the working apparatus according to the ambient power, the adjustment output module is specifically used for determining whether the ambient power value monitored in a preset operating frequency band is greater than a preset ambient power threshold; determining that there is an interference signal, and switching the operating frequency and/or alarm of the working apparatus, when the ambient power value is greater than the preset ambient power threshold; continuing monitoring when the ambient power value is not greater than the preset ambient power threshold;

or, determining whether the ambient power values monitored in the preset operating frequency band within N consecutive communication cycles and/or within a continuous preset duration are all greater than a preset ambient power threshold, wherein N is a positive integer not less than 2 and the preset duration is not less than the duration of 2 communication cycles; determining the presence of an interference signal, and switching the operating frequency and/or alarm of the working apparatus, when the ambient power values are all greater than the preset ambient power threshold; continuing monitoring when the ambient power values are not all greater than the preset ambient power threshold.

In an embodiment, when adjusting the operating state of the working apparatus according to the output power, the adjustment output module is specifically used for determining the relationship between the magnitudes of the monitored output power value and a preset output power threshold; wherein the preset output power threshold comprises a preset first output power threshold and a preset second output power threshold, and the preset second output power threshold is less than the preset first output power threshold;

reducing the output power of the capsule endoscope when the monitored output power value is greater than the first output power threshold;

increasing the output power of the capsule endoscope when the monitored output power value is less than the second output power threshold;

maintaining the monitoring state when the monitored output power value is between the first output power threshold and the preset second output power threshold.

Compared with the prior art, the control method, control system, electronic device and readable storage medium for capsule endoscope of the present invention, has advantages including monitoring the power during the dormant period before image interaction and/or in the process of image interaction, thus adjusting the operating state of the capsule endoscope in real time, which can improve the wireless communication performance and operating time of the capsule endoscope.

DETAILED DESCRIPTION

The present invention can be described in detail below with reference to the accompanying drawings and preferred embodiments. However, the embodiments are not intended to limit the present invention, and the structural, method, or functional changes made by those skilled in the art in accordance with the embodiments are included in the protection scope of the present invention.

The present invention provides a working apparatus, the working apparatus comprising: a capsule endoscope, and an external data recorder that cooperates with and controls the capsule endoscope. The capsule endoscope refers to a capsule-shaped device that can be swallowed into a human body, is usually located in the digestive tract of a subject during examination, and is used for data interaction with the external data recorder, the data including: images taken by the capsule endoscope in the digestive tract, operating parameters and status of the instrument itself, etc.

In addition, in an embodiment of the present invention, a workstation can be optionally provided for recording, processing, and controlling the external data recorder and the capsule endoscope. The workstation can be a server, a personal computer or a display device. The workstation is installed with corresponding operating software that can be used to display images taken by the capsule endoscope and various sensor information, perform complex calculations, and regulate the operating states of the capsule endoscope and the external data recorder.

Figure 1:
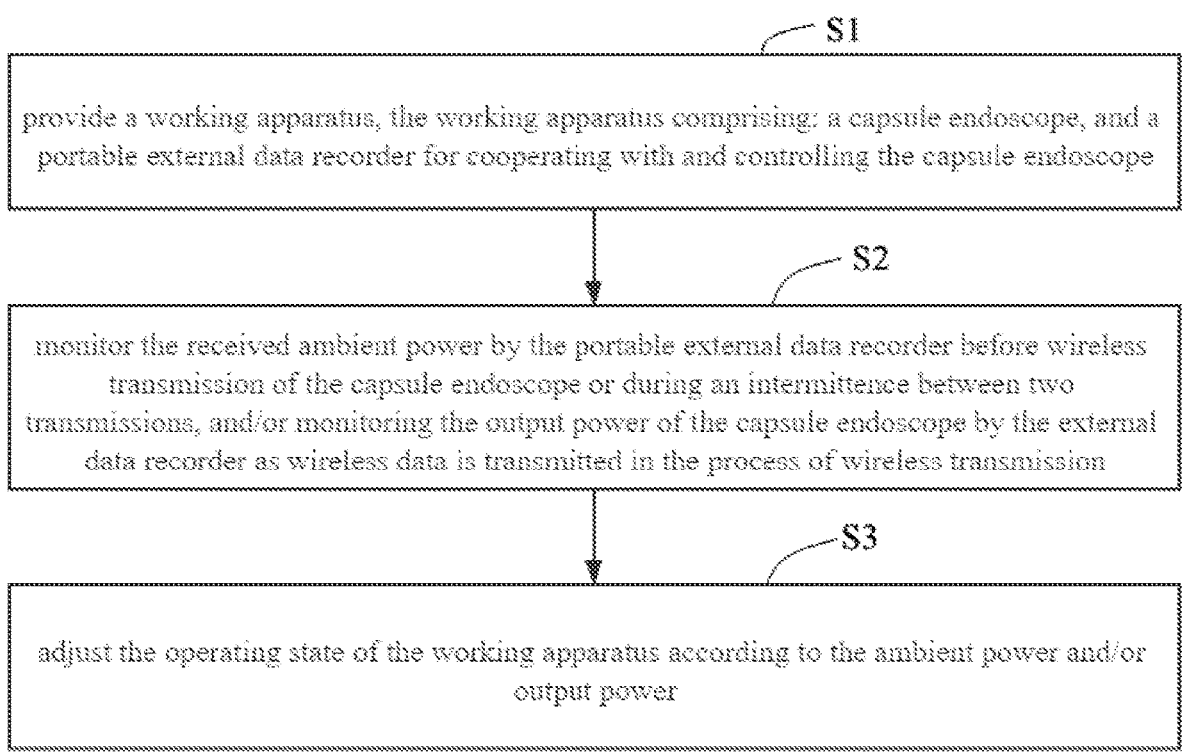
FIG. 1 is a schematic flowchart of a control method for a capsule endoscope according to an embodiment of the present invention.

As shown in FIG. 1, the first embodiment of the present invention provides a control method for a capsule endoscope, and the control method comprises:

step S1, providing a working apparatus, the working apparatus comprising: a capsule endoscope, and a portable external data recorder for cooperating with and controlling the capsule endoscope; step S2, monitoring the received ambient power by the portable external data recorder before wireless transmission of the capsule endoscope or during an intermittence between two transmissions, and/or monitoring the output power of the capsule endoscope by the portable external data recorder as wireless data is transmitted in the process of wireless transmission; step S3, adjusting the operating state of the working apparatus according to the ambient power and/or output power.

Figure 2:
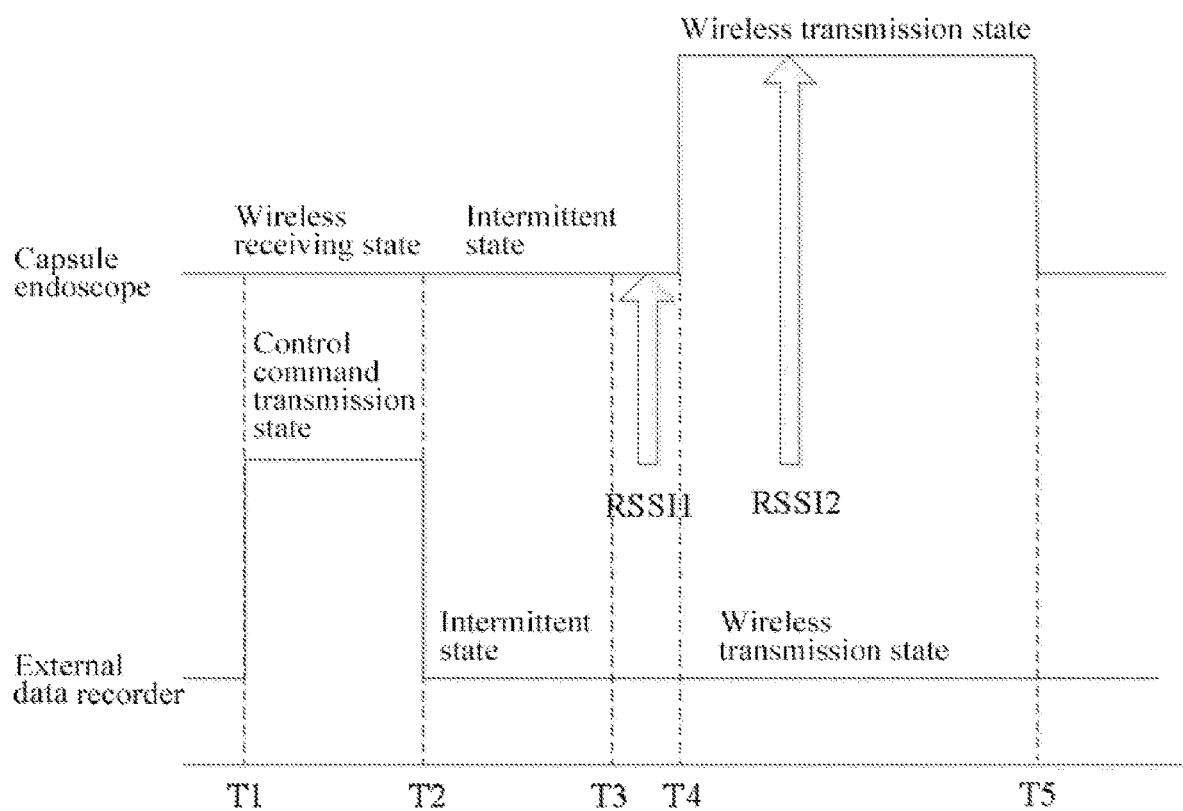
FIG. 2 is an operating sequence diagram of the working apparatus of the present invention.

As shown in FIG. 2, in a communication cycle, the working sequence of the capsule endoscope includes three states: wireless receiving state during the time period T1-T2, intermittent state during the time period T2-T4, in which some tasks that are not related to wireless communication may be executed, and wireless transmission state during the time period T4-T5. The working sequence of the portable external data recorder also includes three states: control command transmission state during the time period T1-T2, intermittent state during the time period T2-T3, and wireless receiving state during the time period T3-T5. In addition, the portable external recorder can also execute power monitoring twice synchronously in the wireless receiving state, execute RSSI1 during the time period T3-T4, and execute RSSI2 during the time period T4-T5.

Once the capsule endoscope starts working, it executes the same sequence in each communication cycle. It should be noted that, according to specific application scenarios, the sequence interval of each communication cycle can be adjusted as needed.

Figure 3:
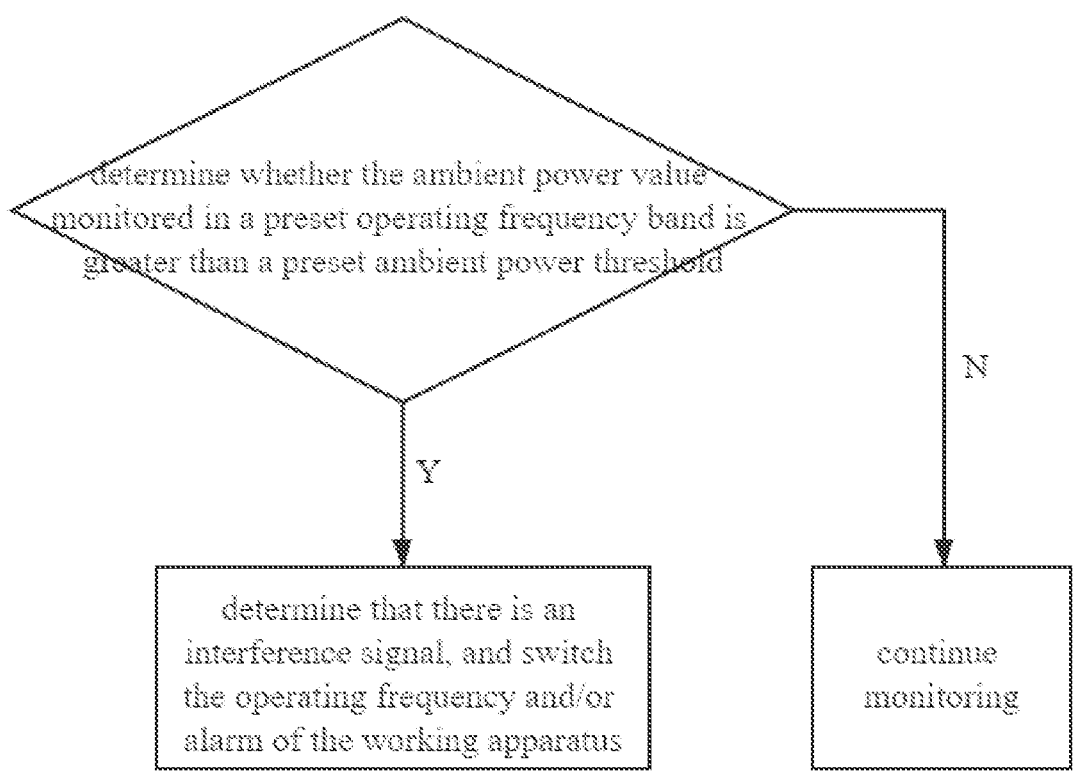
FIG. 3, FIG. 4 and FIG. 5 respectively are schematic diagrams of the specific implementation flow of one of the steps in FIG. 1.

As shown in FIG. 3, in a specific embodiment of the present invention, the step S3 "adjusting the operating state of the working apparatus according to the ambient power" specifically comprises: determining whether the ambient power value monitored in a preset operating frequency band is greater than a preset ambient power threshold; if yes, determining that there is an interference signal, and switching the operating frequency and/or alarm of the working apparatus; if not, continuing monitoring.

Figure 4:
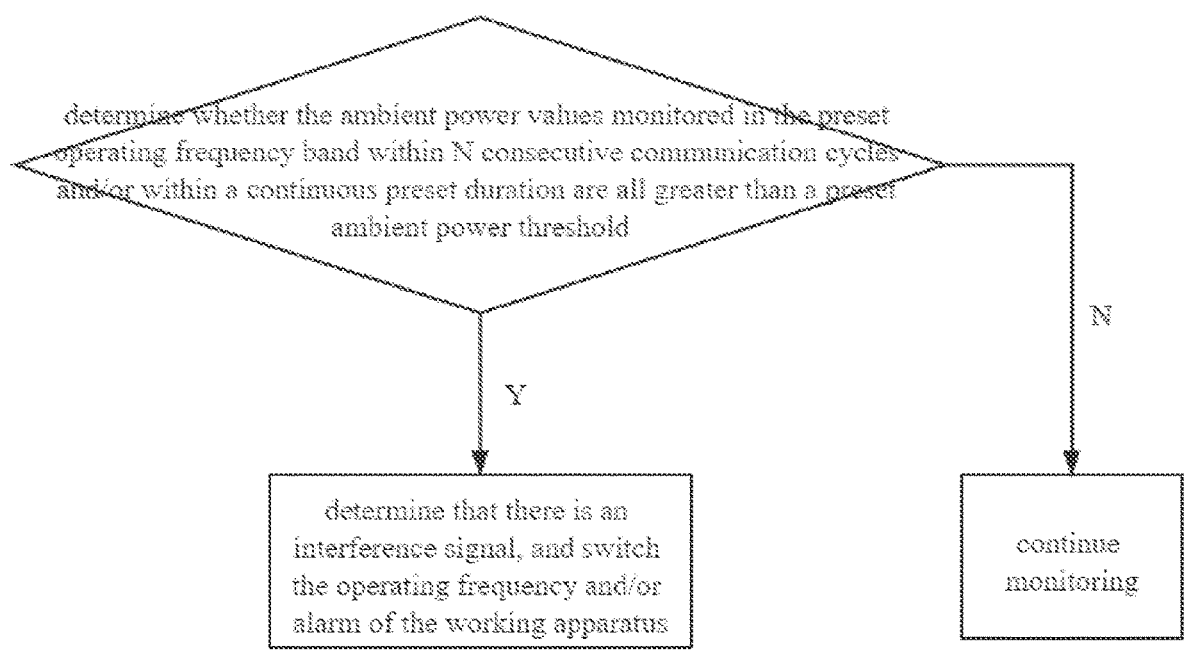

When it is detected that the ambient power value is greater than the preset ambient power threshold, it may be an external instantaneous influence. So, in order to improve the identification accuracy of the device, as shown in FIG. 4, in a preferred embodiment of the present invention, "adjusting the operating state of the working apparatus according to the ambient power" specifically comprises: determining whether the ambient power values monitored in the preset operating frequency band within N consecutive communication cycles and/or within a continuous preset duration are all greater than a preset ambient power threshold, wherein N is a positive integer not less than 2, and the preset duration is not less than the duration of 2 communication cycles; if yes, determining that there is an interference signal, and switching the operating frequency and/or alarm of the working apparatus; if not, continuing monitoring.

The ambient power threshold is a fixed power value, the magnitude of which is related to the operating frequency of the working apparatus. In the specific embodiment of the present invention, the ambient power threshold is greater than the sensitivity of the working apparatus itself, and the difference is, for example, any value in 5 dB-50 dB.

For ease of understanding, here is described a specific example for reference. As shown in FIG. 2, in the time period T3-T4, the capsule endoscope is about to complete image processing such as image compression, and during this period, the capsule endoscope does not transmit a signal to the external data recorder. Thus, when the external data recorder performs power monitoring during this period, the power usually fluctuates in a small range around a fixed value. Take the capsule endoscope and the external data recorder working at 2460 MHz as an example, when there is no interference signal of the same frequency band in the surrounding environment, the power value monitored by the external data recorder is usually less than −100 dBm. At this point, the ambient power threshold can be preset to −75 dBm. Accordingly, when the working apparatus is operating, during the time period T3-T4, the external data recorder monitors the ambient power in real time. Assuming that the currently monitored power value is −70 dBm, which is greater than the preset threshold, it can be determined that there is an interference signal, such as an interference signal from WIFI, microwave ovens, etc. At this point, an alarm signal can be sent to the user by, for example, making a sound, lighting up an indicator, etc. Further, in order to avoid interference signals, the external data recorder can send a frequency switching signal to the capsule endoscope to instruct it to switch operating frequency in a step of, for example, 10 MHz; and when the operating frequency of the working apparatus is switched to 2460+10=2470 MHz, the external data recorder continues monitoring until it is stabilized in a certain frequency band without interference signals.

In a preferred embodiment of the present invention, in order to avoid the impact of a burst of transient pulses on the apparatus, the monitored ambient power can be determined within N consecutive communication cycles and/or within a continuous preset duration, so as to further improve the identification accuracy. For example, if it is determined that the monitored ambient power value is greater than the preset threshold in N consecutive communication cycles and/or in the continuous preset duration, the interference signal is not a transient pulse, but a continuous interference. Then, switching operating frequency of the working apparatus and/or giving an alarm is followed.

According to the embodiment, the control method for capsule endoscope, by comparing the ambient power monitored in real time with the preset ambient power, the external electromagnetic environment data can be obtained indirectly in real time, and the operating frequency of the working apparatus can be automatically switched according to the monitoring result to avoid interference signals. So that it can effectively reduce the loss of images due to external interference during the clinical examination.

Figure 5:
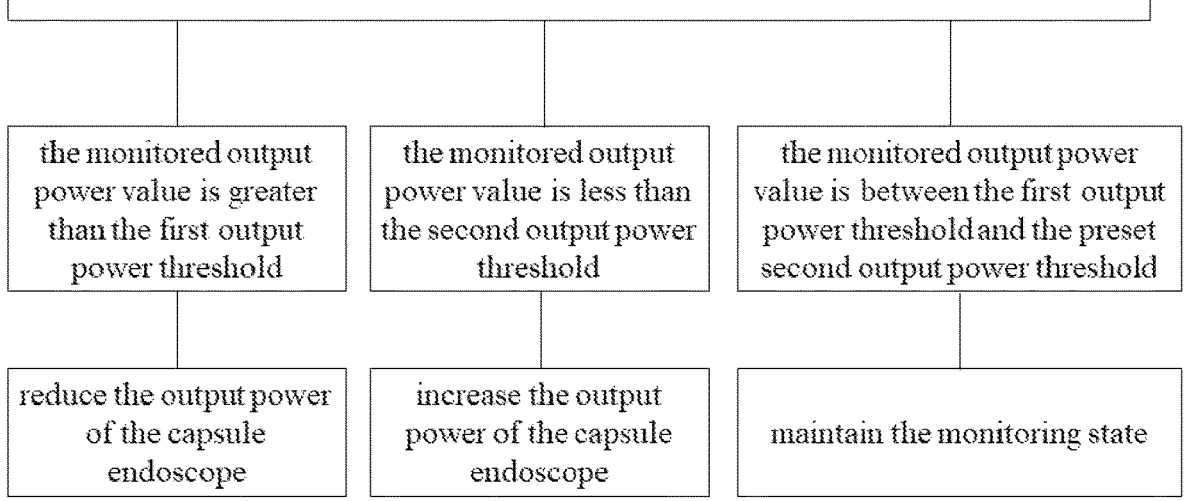

As shown in FIG. 5, in a preferred embodiment of the present invention, the step S3 "adjusting the operating state of the working apparatus according to the output power" specifically comprises: determining the relationship between the magnitudes of the monitored output power value and a preset output power threshold. The preset output power threshold includes: a preset first output power threshold and a preset second output power threshold, wherein the preset second output power threshold is less than the preset first output power threshold. Reduce the output power of the capsule endoscope when the monitored output power value is greater than the first output power threshold; increase the output power of the capsule endoscope when the monitored output power value is less than the second output power threshold; maintain the monitoring state when the monitored output power value is between the first output power threshold and the preset second output power threshold.

The preset first output power threshold and the preset second output power threshold are both a fixed value, which is the fluctuation value of the preset output power threshold. The magnitude of the preset output power threshold is related to the receiving sensitivity of the external data recorder. In the specific embodiment of the present invention, the preset output power threshold is greater than the receiving sensitivity of the external data recorder, with the difference being, for example, any value from 5 dB to 50 dB. Accordingly, the preset first output power threshold=the preset output power threshold+X dB, the preset second output power threshold=the preset output power threshold −X dB, the unit of X is dB, which is a constant, for example, X is 2 dB.

For ease of understanding, here is described a specific example for reference. As shown in FIG. 2, during the time period T4-T5, the capsule endoscope continuously sends the captured images to the external data recorder in the form of wireless signals, and at the same time, the external data recorder receives the image signals. During this period, the external data recorder monitors the output power of the capsule endoscope while the image signal is sent. Assuming the test sensitivity of the data recorder is −80 dBm, the preset output power threshold can be set to −70 dBm, and accordingly, the preset first output power threshold is −68 dBm, and the preset second output power threshold is −72 dBm. When the output power is monitored during this period, due to the difference in human tissue thickness and electrical parameters, the capsule output power received by the external data recorder may fluctuate within a certain range while the capsule endoscope passes through different regions in the digestive tract. When the working apparatus is operating, during the time period T5-T7, the external data recorder can monitor the output power of the capsule endoscope in real time when it transmits image signals. Assuming that the currently monitored output power value is −65 dBm, which is greater than the preset first output power threshold, it means that the current link margin is large. At this point, the external data recorder sends a control command signal to the capsule endoscope to decrease the output power of the capsule endoscope, for example: to decrease the output power of the capsule endoscope by 5 dBm. Assuming that the currently monitored output power value is −71 dBm, which is between the preset first output power threshold and the preset second output power threshold, it means that the current link margin is appropriate. At this point, maintain the output power of the capsule endoscope. Assuming that the currently monitored output power value is −75 dBm, which is less than the preset second output power threshold, it means that the current link margin is small. At this point, the external data recorder sends a control command signal to the capsule endoscope to increase the output power of the capsule endoscope, for example: to increase the output power of the capsule endoscope by 5 dBm.

The link margin in this embodiment, refers to the rich dB value of the wireless signal power actually received at the receiver compared with the minimum allowable receiving threshold of the receiver (usually the receiver's sensitivity) in a wireless communication system.

In this embodiment, the external data recorder monitors the ambient power in real time during the time period T3-T4 to ensure that there is no signal interference of the same frequency from the outside.

The control command signal in this embodiment is sent by the external data recorder. The capsule endoscope can perform corresponding actions according to the received command, for example, taking images, switching the operating frequency, adjusting the output power of the capsule endoscope, and adjusting the capturing frames of the capsule endoscope, etc.

Further, in a preferred embodiment of the present invention, since an addition dynamic adjustment mechanism of the output power of the capsule endoscope, a PA chip can be added to the capsule endoscope, so that the capsule endoscope can further increase the output power as needed. The output power can be increased directly by starting the PA chip. Correspondingly, the method further comprises: starting the PA chip when the output power of the capsule endoscope needs to be increased.

The PA chip of the present invention, can increase the output power of the capsule endoscope by 5~7 dB. It should be noted that, although the power consumption of the capsule endoscope is increased at the maximum output power (within about 30% of the time), but in more time (about 70% of the time), the output power of the capsule endoscope is reduced, and accordingly, its power consumption is also reduced. In this way, the overall operating time of the capsule endoscope is extended by 5~10% instead.

The control method for capsule endoscope of this embodiment, depending on the output power dynamic adjustment mechanism, keep the link margin of the working apparatus in a reasonable range while ensuring a good communication between the capsule endoscope and the portable external data recorder, so that it can cover the people of larger size, and extend the overall operating time of the capsule endoscope by 5-10%.

Further, the present invention provides an electronic device comprising a memory and a processor. The memory stores a computer program that can run on the processor, and the processor executes the program to implement the steps of the control method for capsule endoscope described above.

Further, the present invention provides a computer-readable storage medium for storing a computer program. The computer program is executed by the processor to implement the steps of the control method for capsule endoscope described above.

Figure 6:
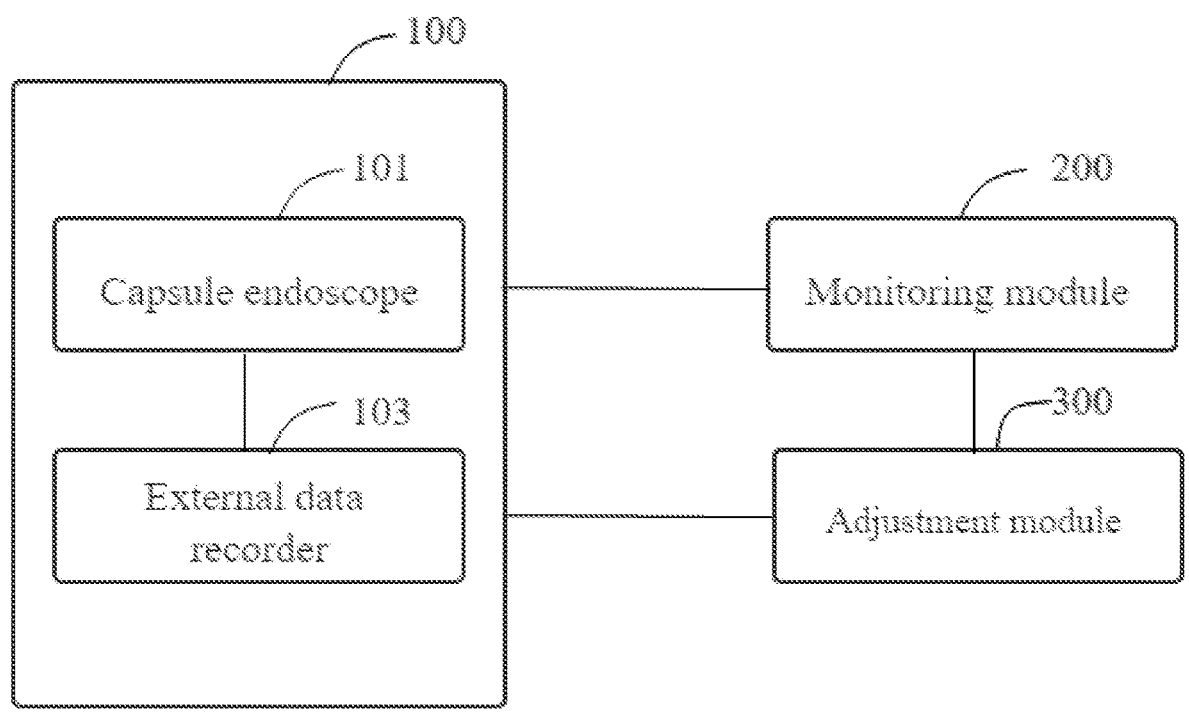
FIG. 6 is a block diagram of a control system for a capsule endoscope according to an embodiment of the present invention.

As shown in FIG. 6, an embodiment of the present invention provides a control system for capsule endoscope, the system comprising: a working apparatus 100, a monitoring module 200, and an adjustment output module 300. Wherein the working apparatus 100 comprises: a capsule endoscope 101, and a portable external data recorder 103 for cooperating with and controlling the capsule endoscope 101.

In the specific embodiments of the present invention, the monitoring module 200 is used for monitoring the received ambient power by the portable external data recorder 103 before wireless transmission of the capsule endoscope 101 or during an intermittence between two transmissions, and/or monitoring the output power of the capsule endoscope 101 by the portable external data recorder 103 as wireless data is transmitted in the process of wireless transmission.

The adjustment output module 300 is used for adjusting the operating state of the working apparatus according to the ambient power and/or output power.

In a preferred embodiment of the present invention, when the adjustment output module 300 adjusts the operating state of the working apparatus according to the ambient power, it is specifically used for: determining whether the ambient power value monitored in a preset operating frequency band is greater than a preset ambient power threshold; if yes, determining that there is an interference signal, and switching the operating frequency and/or alarm of the working apparatus; if not, continuing monitoring;

When the adjustment output module 300 adjusts the operating state of the working apparatus according to the ambient power, it is specifically used for: determining whether the ambient power values monitored within N consecutive communication cycles and/or within a continuous preset duration are all greater than a preset ambient power threshold, wherein N is a positive integer not less than 2, and the preset duration is not less than the duration of 2 communication cycles; if yes, determining that there is an interference signal, and switching the operating frequency and/or alarm of the working apparatus; if not, continuing monitoring.

In a preferred embodiment of the present invention, when the adjustment output module 300 adjusts the operating state of the working apparatus according to the output power, it is specifically used for: determining the relationship between the magnitudes of the monitored output power value and a preset output power threshold. The preset output power threshold includes: a preset first output power threshold and a preset second output power threshold, wherein the preset second output power threshold is less than the preset first output power threshold. Reduce the output power of the capsule endoscope 101 when the monitored output power value is greater than the first output power threshold; increase the output power of the capsule endoscope 101 when the monitored output power value is less than the second output power threshold; maintain the monitoring state when the monitored output power value is between the first output power threshold and the preset second output power threshold.

Those skilled in the art can clearly understand that, for the convenience and conciseness of the description, the specific working process of the system described above is not repeated as the corresponding process has been detailed in the foregoing method implementation which can be referred to.

In summary, the control method, control system, electronic device and readable storage medium for capsule endoscope of the present invention, has advantages including monitoring the power during the dormant period before image interaction between the capsule endoscope and the external data recorder, and/or in the process of image interaction, thus adjusting the operating state of the capsule endoscope in real time, which can improve the wireless communication performance and operating time of the capsule endoscope.

For the convenience of description, the device is described in various modules divided by functions separately. When implementing the present invention, the functions of the various modules can be implemented in the same or different software and/or hardware.

The device implementations described above are merely illustrative. The modules described as separate components may or may not be physically separated, and the components displayed as modules may or may not be physical modules, that is, they may be located in one place, or may also be distributed over a plurality of network modules. Some or all of the modules may be selected according to actual needs to achieve the object of the embodiment. It can be understood and implemented by ordinary persons skilled in the art without creative work.

It should be understood that, although the specification is described in terms of embodiments, not every embodiment merely comprises an independent technical solution. This narration in the specification is only for clarity. Those skilled in the art should have the specification as a whole, and the technical solutions in each embodiment may also be combined as appropriate to form other embodiments that can be understood by those skilled in the art.

The series of detailed descriptions listed above are only specific descriptions of the feasible embodiments of the present invention, and are not intended to limit the protection scope of the present invention. Any equivalent embodiments or variations made without departing from the technical spirit of the present invention should be included in the protection scope of the present invention.

What is claimed is:

1. A control method for a capsule endoscope, comprising:
providing a working apparatus, the working apparatus comprising: a capsule endoscope, and a portable external data recorder for cooperating with and controlling the capsule endoscope;
monitoring the received ambient power by the portable external data recorder before wireless transmission of the capsule endoscope or during an intermittence between two transmissions, or
monitoring the received ambient power by the portable external data recorder before wireless transmission of the capsule endoscope or during an intermittence between two transmissions and monitoring the output power of the capsule endoscope by the external data recorder as wireless data is transmitted in the process of wireless transmission;
adjusting an operating state of the working apparatus according to the received ambient power or
adjusting an operating state of the working apparatus according to the received ambient power and output power, comprising steps of:
determining whether the ambient power values monitored in the preset operating frequency band within N consecutive communication cycles and/or within a continuous preset duration are all greater than a preset ambient power threshold, wherein N is a positive integer not less than 2 and the preset duration is not less than the duration of 2 communication cycles;
determining that there is an interference signal, and switching the operating frequency and/or alarm of the working apparatus, when the ambient power values are all greater than the preset ambient power threshold; and
continuing monitoring when the ambient power values are not all greater than the preset ambient power threshold.

2. The method of claim 1, wherein the step of "adjusting the operating state of the working apparatus according to the ambient power" further comprising:
determining whether the ambient power value monitored in a preset operating frequency band is greater than a preset ambient power threshold;
determining that there is an interference signal, and switching the operating frequency and/or alarm of the working apparatus, when the ambient power value is greater than the preset ambient power threshold;
continuing monitoring when the ambient power value is not greater than the preset ambient power threshold.

3. The method of claim 1, wherein the step of "adjusting the operating state of the working apparatus according to the output power" further comprises:
determining the relationship between the magnitudes of the monitored output power value and a preset output power threshold; wherein the preset output power threshold comprises a preset first output power threshold and a preset second output power threshold and the preset second output power threshold is less than the preset first output power threshold;
reducing the output power of the capsule endoscope when the monitored output power value is greater than the first output power threshold;
increasing the output power of the capsule endoscope when the monitored output power value is less than the second output power threshold;

maintaining the monitoring state when the monitored output power value is between the first output power threshold and the preset second output power threshold.

4. The method of claim 3, wherein capsule endoscope further comprises a power amplifier chip, and the method further comprising: starting the power amplifier chip when the output power of the capsule endoscope needs to be increased.

5. A computer-readable storage medium storing computer programs, wherein the computer programs can be executed by a processor to implement the steps in a capsule endoscope control method, wherein the method comprises:
providing a working apparatus, the working apparatus comprising: a capsule endoscope, and a portable external data recorder for cooperating with and controlling the capsule endoscope;
monitoring the received ambient power by the portable external data recorder before wireless transmission of the capsule endoscope or during an intermittence between two transmissions, and/or monitoring the output power of the capsule endoscope by the external data recorder as wireless data is transmitted in the process of wireless transmission;
adjusting the operating state of the working apparatus according to the ambient power and/or output power.

6. A control system for a capsule endoscope, comprising:
a working apparatus, the working apparatus comprising: a capsule endoscope, and a portable external data recorder for cooperating with and controlling the capsule endoscope;
a monitoring module, for monitoring the received ambient power by the portable external data recorder before wireless transmission of the capsule endoscope or during an intermittence between two transmissions, or
monitoring the received ambient power by the portable external data recorder before wireless transmission of the capsule endoscope or during an intermittence between two transmissions and;
adjusting an operating state of the working apparatus according to the received ambient power or
adjusting an operating state of the working apparatus according to the received ambient power and output power;
when adjusting the operating state of the working apparatus according to the ambient power, the adjustment output module is configured to determine whether the ambient power value monitored in a preset operating frequency band is greater than a preset ambient power threshold; determining that there is an interference signal, and switching the operating frequency and/or alarm of the working apparatus, when the ambient power value is greater than the preset ambient power threshold; continuing monitoring when the ambient power value is not greater than the preset ambient power threshold; or determining whether the ambient power values monitored in the preset operating frequency band within N consecutive communication cycles and/or within a continuous preset duration are all greater than a preset ambient power threshold, wherein N is a positive integer not less than 2, and the preset duration is not less than the duration of 2 communication cycles; determining that there is an interference signal, and switching the operating frequency and/or alarm of the working apparatus, when the ambient power values are all greater than the preset ambient power threshold; continuing monitoring when the ambient power values are not all greater than the preset ambient power threshold.

7. The system of claim 6, wherein when adjusting the operating state of the working apparatus according to the output power, the adjustment output module is configured to determine the relationship between the magnitudes of the monitored output power value and a preset output power threshold; wherein the preset output power threshold comprises a preset first output power threshold and a preset second output power threshold, and the preset second output power threshold is less than the preset first output power threshold;
reducing the output power of the capsule endoscope when the monitored output power value is greater than the first output power threshold;
increasing the output power of the capsule endoscope when the monitored output power value is less than the second output power threshold;
maintaining the monitoring state when the monitored output power value is between the first output power threshold and the preset second output power threshold.

* * * * *

UNITED STATES PATENT AND TRADEMARK OFFICE
CERTIFICATE OF CORRECTION

PATENT NO.         : 11,582,386 B2
APPLICATION NO.    : 17/150788
DATED              : February 14, 2023
INVENTOR(S)        : Weikang He et al.

Page 1 of 1

It is certified that error appears in the above-identified patent and that said Letters Patent is hereby corrected as shown below:

On the Title Page

Item (73) should be:
Ankon Technologies Co., LTD. Wuhan (CN);
ANX IP Holding PTE. LTD, Singapore (SG).

Signed and Sealed this
Sixth Day of August, 2024

Katherine Kelly Vidal
*Director of the United States Patent and Trademark Office*